United States Patent [19]

Ghadjar et al.

[11] Patent Number: 5,207,681
[45] Date of Patent: May 4, 1993

[54] DRILL GUIDE APPARATUS FOR PERPENDICULAR PERFORATION OF THE CRANIUM

[75] Inventors: Fathali G. Ghadjar; Jamshid B. G. Ghajar; Robert J. Hariri, all of New York, N.Y.

[73] Assignee: Neurodynamics, Inc., New York, N.Y.

[21] Appl. No.: 424,034

[22] Filed: Oct. 19, 1989

Related U.S. Application Data

[63] Continuation-in-part of Ser. No. 113,580, Oct. 26, 1987, abandoned.

[51] Int. Cl.⁵ .............................................. A61B 17/16
[52] U.S. Cl. ........................................ 606/96; 606/180
[58] Field of Search ................... 606/80, 96, 179, 180; 408/95, 97, 112

[56] References Cited

U.S. PATENT DOCUMENTS

| | | | |
|---|---|---|---|
| 1,603,359 | 10/1926 | Schneckloth | 408/112 |
| 2,155,527 | 4/1939 | Brandt | 408/112 X |
| 2,294,303 | 8/1942 | Jagow | 128/92 VD |
| 2,401,548 | 6/1946 | Chapman | 128/310 |
| 3,017,887 | 1/1962 | Heyer | |
| 3,073,310 | 1/1963 | Mocarski | |
| 3,833,313 | 9/1974 | Gallion | 408/112 |
| 4,012,161 | 3/1977 | Shultz | 408/112 X |
| 4,375,341 | 3/1983 | Schulze | 408/97 X |
| 4,605,345 | 8/1986 | Giughese | 408/95 |
| 4,735,528 | 4/1988 | Parrone | 408/112 X |

OTHER PUBLICATIONS

Ghajar, A Guide for Ventricular Catheter Placement, J. Neurosurg. 63: 985–986 (1985).
Instruction Manual for Ghajar device described in Ref. AR.
Cooper, The Neurosurgical Alleviation of Parkensonism, Chemopallidectomy, p. 83 (1956).
Kandall, A Trephine Needle for Vertebral Body Biopsy, the Lancet, Feb. 27, 1960, p. 474.

*Primary Examiner*—Michael H. Thaler
*Attorney, Agent, or Firm*—Pennie & Edmonds

[57] ABSTRACT

An apparatus and method for drilling an orifice in a human cranium at an angle of substantially 90° to a plane defined by a tangent to the surface of the cranium at the orifice. The apparatus comprises a ring structure adapted to guide and support a drill, the ring structure comprising a retaining member configured for engagement with a flexible member such as a spring and a sleeve member configured for insertion within the retaining member and operatively associated therewith to form a support assembly. The support assembly is capable of a restricted degree of vertical, slideable movement within a tubular member. The apparatus further comprises a tubular member, adjacent and external to the ring structure, adapted to guide and support the support assembly; a flexible member adjacent the support assembly for restricting vertical movement thereby within the tube; and support structure, the support structure being adapted to rest unsecured upon the cranium. The method of the invention comprises positioning the drill guide upon the patient's cranium such that the support structure, the tubular member and the support assembly are related to each other and to the cranium so as to guide the drill through the cranium in a direction perpendicular to a plane defined by a tangent to the surface of the cranium at the orifice and drilling through said cranium until the tip of the drill bit passes therethrough and stops rotation rapidly once it has penetrated the surface.

12 Claims, 5 Drawing Sheets

DRILL GUIDE APPARATUS FOR PERPENDICULAR PERFORATION OF THE CRANIUM

This is a continuation-in-part of application Ser. No. 07/113,580, filed Oct. 26, 1987, now abandoned.

TECHNICAL FIELD

The invention relates to a method and apparatus for guiding a drilling device so as to penetrate a human cranium at an angle of 90° to a plane tangent to the surface thereof. More particularly, the invention relates to a drill guide having a clutch mechanism and re-start capability utilized to control and direct a rotating drill bit during surgical procedures requiring the formation of one or more "burr" holes in the skull.

BACKGROUND OF THE INVENTION

Surgeons practicing in the field of neurosurgery have been aware for a number of years of the importance of perforating a patient's cranium at an angle of substantially 90° to a plane tangent to the surface thereof. The purpose behind this requirement is actually twofold: first, a burr hole drilled at an orientation of 90° to the surface of the skull prevents injury to the underlying dura and brain tissue which may otherwise be caused due to the continued rotation of the metal bit of the drilling apparatus once the bit tip exits the skull.

That is to say that, at an orientation of other than 90°, the drill bit of drilling devices in current use often continues to rotate after the tip portion has pierced the cranium, despite the incorporation of a standard, safety clutch mechanism commonly utilized with these drilling devices. The operation of this standard clutch is such that the drill should automatically stop rotating once the pressure upon the tip of the bit is released, i.e., once the tip of the bit passes entirely through the cranium.

In current state of the art drills, a secondary drill hole is used to prevent forward motion of a drill bit ("plunging") once the cranium has been penetrated. This secondary hole is made by using two concentric dill bits, that is, a primary bit is positioned inside a secondary bit. The secondary hole forms a platform which prevents forward motion once both the primary and secondary drill bits stop rotating.

The type of drill bit commonly utilized during neurological procedures, however, comprises an outer sleeve and a slideable inner sleeve, partially rotatable within the outer sleeve, which extends a minimal distance beyond the outer sleeve. If the burr hole is oriented at some angle other than 90°, while the trailing edges upon the outer sleeve of the bit are still engaging the bony surface of the patient's skull, the grinding surfaces upon the inner sleeve, which extend beyond those of the outer sleeve as noted above, can and often do cause serious injury to the underlying tissue within the cranial cavity.

In contrast, however, a burr hole aligned at an angle of substantially 90° to the surface of the skull permits the clutch mechanism to operate properly and thus stops the rotation of the entire bit once the tip has penetrated the bone, preventing accidental injury to the brain and related tissues.

The second and no less important general purpose behind providing a burr hole at an angle of substantially 90° to the surface of the skull is to ensure that a ventricular catheter subsequently inserted into the brain, perpendicular to the curvature of the cranium, will not deviate from its intended path due to a misaligned skull hole. Standard procedures for ventricular catherization are disclosed in the textbook literature (see, for example, *Neurosurgery*, edited by Robert H. Wilkins and Setti S. Rengachary, Section A, Chapter 13, "Techniques of Ventricular Puncture" (McGraw-Hill 1984).

A recently developed apparatus and procedure for ensuring correct catheter placement was, in fact, disclosed and claimed by one of the present applicants in U.S. Pat. No. 4,613,324, issued Sep. 23, 1986. The apparatus comprises a guide assembly which, when positioned over an orifice (previously drilled by other means) above the anterior horn of the lateral ventricle in the cranium, guides a catheter and obdurator through the orifice and into the lateral ventricle at an angle normal to an imaginary plane formed by a tangent to the cranium at the orifice.

Although, as discussed above, the importance of orienting one or more burr holes at an angle of substantially 90° to the surface of the patient's skull during such a surgical procedure is well-known, there is currently no relevant art of which the applicants are aware which teaches how this burr hole through the patient's cranium can be prepared and aligned so as to extend through the skull at an angle of substantially 90° to the surface thereof. The difficulty in producing such a precisely aligned burr hole has thus led to the search for a rapid, simple, inexpensive and accurate method and apparatus for perforating the patient's cranium at the required angle.

Another drawback of current perforators is their lack of re-start capability, that is, the ability to re-start the drill if drilling should stop prior to penetration of the cranium.

Current perforators incorporate a straight slot on the drive stem which engages a pin holding the inner and outer sleeves of the perforator together. The inner sleeve is also spring loaded thus allowing it to move along the axis of the perforator. The mechanism works provided that the inner drill is pressed against the drive stem by the pressure of the skull bone against its tip and subsequent compression of the spring. Once this pressure is relieved either by penetration of the inner table of the skull or by the surgeon relaxing the force on the perforator, the spring forces the drive stem to disengage from the inner drill, thereby preventing any further perforator penetration. Thus, the current design requires a surgeon to remove the apparatus from the burr hole and manually re-align the inner and outer drill sleeves with the drive stem before re-drilling can begin. While it is imperative that the perforator stop immediately after penetration of the inner table of the skull to prevent damaging the dura or the cortex, it is also important that the surgeon be able to stop and start drilling before completing the burr-hole.

SUMMARY OF THE INVENTION

An object of the present invention is to provide a device which offers a surgeon a greater degree of control over a drill bit during an operation involving the perforation of the cranium. The guide of the present invention prevents the drill bit from skipping on the bone of the skull, especially at the start of the drilling operation. The guide also acts as a guard to prevent the surgeon or other operating room personnel from touching the rotating bit and injuring themselves.

In addition, use of the guide described herein prevents the edges of the scalp or swabs used during the operation from coming close to the drill bit during perforation, thus preventing injury to the scalp and ensuring that bandages and other operating material do not wrap themselves around the drill bit as it spins.

A further object of the present invention is to provide a method and apparatus for perforating a human cranium at an angle of substantially 90° to an imaginary plane tangent to the cranium at the orifice. This 90° angle of penetration permits the safety clutch mechanism in the drill (which is not part of the present invention) to operate correctly and thus stop the rotation of the bit once it has passed through the cranial bone. This prevents accidental injury to the underlying dura and brain tissue.

An additional object of the present invention is to provide a drill guide apparatus which can be manufactured cheaply and used as a disposable item. Thus, the surgeon can be supplied with a sharp, sterilized drill for accurate penetration of the skull for each patient. The use of a sharp drill for perforating reduces the operating time as well as undue stress to the patient.

A further object of the present invention is to provide a drill guide apparatus equipped with a drive shaft and a clutch mechanism having a dynamic brake which stops rotation and prevents plunging of the drill bit as soon as the bit penetrates the cranium. The dynamic brake comprises a tubular member having a plurality of sprocket members which are separated from one another by ring members. The sprocket members have a plurality of outwardly extending sprockets. By coupling the tubular member to the drive shaft, the sprocket members rotate inside a cylindrical member having inwardly projecting ratchet teeth which are designed to engage the sprockets. As long as the tubular member is rotating with the drive shaft, the sprockets force the ratchet teeth outward so that the tubular member can rotate freely and move forward. As soon as the tubular member stops rotating, however, the ratchet teeth return to their original position, thus preventing forward motion by engaging the ring members separating the sprocket members. This configuration quickly and efficiently stops the drill bit from rotating and eliminates drill bit plunging without requiring a secondary hole. Thus, a physician can drill a single, small, clean hole with a minimum risk of plunging.

Another object of the present invention is to provide a drill guide apparatus having re-start capability. Preferably this object is accomplished by having a drive shaft configured and designed to permit rapid re-alignment of the drive shaft with the retaining pin thereby re-coupling the drive shaft with the drill bit.

An additional object of the present invention is to provide a drill guide apparatus which has re-start capability and which prevents rotation and forward motion of the drill bit as soon as a first end of the drill bit penetrates the cranium. Preferably, the drill guide is equipped with a drive shaft configured and designed to permit re-alignment of the components, and a clutch mechanism for rapidly attaching different drill bits thereto. This apparatus allows the physician the versatility to select the required size and/or shape of drill bit necessary for a particular operation; position the drill to ensure that the cranium will be perforated at an angle of substantially 90° to an imaginary plane tangent to the cranium at the point of drilling; start and re-start the drill without removing the apparatus from the burr hole; and perforate the cranium without injuring the underlying brain tissue.

A first embodiment of the present invention comprises an apparatus for accurately and reproducibly guiding a drill during the preparation of an orifice in a human cranium. The orifice should extend (as described above) at an angle of substantially 90° to a plane defined by a tangent to the cranium at the orifice. The apparatus comprises: ring means adapted to guide and support the drill, the ring means being capable of a restricted degree of vertical, slideable movement within a tubular member; a tubular member, adjacent and external to the ring means, adapted to guide and support the ring means; a flexible member located external to and adjacent the ring means for restricting vertical movement by the ring means within the tubular member; and a support for the tubular member, the support being adapted to rest unsecured upon the cranium. The support, the tubular member and the ring means being related to each other and to the cranium so as to guide the drill through the cranium in a direction perpendicular to a plane defined by a tangent to the cranium.

The apparatus described above may further comprise a drive shaft, means for securing a drill bit, and clutch means rotatably coupling the drive shaft with the drill bit securing means. In this embodiment the clutch means is designed to uncouple the drive shaft from the securing means when a first end of the drill bit has penetrated the cranium, thereby preventing subsequent rotation and forward movement of the drill bit.

The drive shaft is equipped with an upper end adapted to engage a surgical drill and a hollow lower end having a pair of diametrically opposed recesses. The drill bit securing means is equipped with an upper end adapted to mate with the hollow lower end of the drive shaft and a lower end adapted to receive and secure a drill bit. The upper end is further equipped with a pair of diametrically opposed openings.

The clutch means, in this embodiment, comprises a resilient means positioned between the drive shaft and the drill bit securing means which urges the securing means from engagement with the drive shaft. The clutch means further includes providing the ring means with a retaining flange configured and adapted for engagement with the upper portion of the flexible means, and a sleeve portion having diametrically opposed openings and a plurality of sprocket members. The sprocket members include a plurality of outwardly extending sprockets, the sprocket members being separated from another by ring members.

The clutch means also includes a retaining pin which is insertable through the openings of the ring means, as well as insertable through the openings of the drill bit securing means and the drive shaft recesses. This retaining pin rotatably couples the ring means, the drill bit retaining means, and the drive shaft.

A tubular member is provided which surrounds the sleeve portion of the ring means and further includes a plurality of ratchet members having inwardly extending ratchet teeth for mating engagement with the sprockets of the sprocket members. In this embodiment, once a first end of the drill bit has penetrated the cranium, the resilient means urges the drill bit securing means away from the drive shaft a sufficient distance to disengage the retaining pin from the drive shaft recesses. The disengagement of the retaining pin uncouples the drill bit securing means from the drive shaft to prevent further rotation of the drill bit. Furthermore, the ratchet teeth engage the ring members separating the sprocket members to prevent forward movement of the drill bit securing means once it is uncoupled from the drive shaft.

The apparatus described above may additionally comprise a collar member surrounding an upper surface of a bit portion of the drill so as to facilitate rotation of the bit portion within the ring means. This collar member may have grooved portions extending longitudinally along an outer periphery thereof to facilitate insertion of the bit portion within the collar member.

In an alternate embodiment, the ring means comprises a retaining member configured and adapted for engagement with a terminal portion of the flexible member, and a sleeve member, insertable within the retaining member and operatively associated therewith. The retaining member and the sleeve member together form an assembly capable of a restricted degree of vertical movement within the tubular member of the guide.

The sleeve member comprises an open tubular body portion having a first end and a second end, as well as a circular flange member located along an outer peripheral portion of the first end. This flange member is supported upon an upper surface of the retaining member. In addition, the upper surface of the collar member may further comprise an additional flange member, adapted for support upon the flange member of the sleeve. In the preferred embodiment, the sleeve member and the retaining member together form an assembly which is fabricated from a self-lubricating thermoplastic composition in order to facilitate the movement thereof within the tubular member.

The tubular member of this embodiment further comprises means for directing the vertical, slideable movement of the assembly therein. This directing means comprises a smooth, cylindrical surface, formed integrally with a base portion of the tubular member and extending from the base portion into an interior portion of the tubular member.

In a further embodiment, the flexible member is a spring, capable of resisting movement of the assembly toward the base portion of the tubular member. This movement is attributable to downward pressure exerted by the drill during the formation of the orifice. The spring is normally located adjacent and external to the body portion of the sleeve member. Alternately, however, the body portion of the sleeve may be formed integrally with the spring. Additionally, the supports for the guide apparatus comprise a plurality of leg members extending from and formed integrally with a lower surface of the base portion of the tubular member.

A still further embodiment of the invention comprises an apparatus for accurately and reproducibly guiding a drill during the preparation of an orifice in a human cranium. The orifice extends at an angle of substantially 90° to a plane defined by a tangent to the cranium at the orifice. The apparatus comprises: a retaining member configured and adapted for engagement with a terminal portion of spring means and a sleeve member, insertable within the retaining member and operatively associated therewith. The sleeve member comprises an open tubular body portion having a first end, a second end and a circular flange member. The flange member is located along an outer peripheral portion of the first end. The sleeve member and the retaining member together form a guide assembly which is capable of a restricted degree of vertical, slideable movement within a tubular member and is fabricated from a self-lubricating thermoplastic composition to facilitate the movement thereof.

The apparatus further comprises a tubular member adjacent and external to the assembly which is adapted to guide and support both the sleeve and the retaining member. The tubular member has means for directing the vertical slideable movement of the assembly. This directing means comprises a smooth, cylindrical surface, formed integrally with a base portion of the tubular member, which extends from the base portion into an interior portion of the tubular member. Additionally, a spring is located external to and adjacent the body portion of the sleeve. This spring is capable of resisting vertical downward movement of the assembly toward a base portion of the tubular member, caused due to downward pressure exerted by the drill during the formation of the orifice.

The embodiment described above may additionally comprise a plurality of leg members extending from and formed integrally with a lower surface of the base portion of the tubular member. These leg members are adapted to rest unsecured upon the cranium. The tubular member, guide assembly and the leg members are related to each other and to the cranium in a direction perpendicular to a plane defined by a tangent to the cranium. Each of the leg members described above terminates in a free end, the free ends forming a polygon defining a plane. The guide assembly therefore guides the drill in a direction perpendicular to the plane and through the geometric center of the resultant polygon.

In a specific embodiment, the guide support may comprise three legs of equal length. An equilateral triangle is therefore formed by the free end of these legs.

The apparatus described above may further comprise a cap member for interlocking engagement with an upper surface of the tubular member. The cap member has an open bore portion to permit passage of the drill therethrough.

Another embodiment of the invention comprises an apparatus for accurately and reproducibly guiding a drill during the preparation of an orifice in a human cranium. The orifice extends at an angle of substantially 90° to a plane defined by a tangent to the cranium at the orifice. The apparatus comprises: a retaining ring, configured and adapted for engagement with a terminal portion of a flexible spring member and fabricated of a self-lubricating thermoplastic composition; a sleeve also fabricated from a self-lubricating thermoplastic, having an open tubular body portion, the body portion comprising a first end a second end, and a circular flange located along an outer peripheral portion of the first end. The sleeve is insertable within the retaining ring to form a support assembly. This assembly is capable of a restricted degree of vertical, slideable movement within a tubular member.

The apparatus further comprises a tubular member adjacent and external to the support assembly, adapted to guide and support the assembly. The tubular member has means to direct the vertical, slideable movement of the assembly. This directing means comprises a smooth, cylindrical surface, formed integrally with a base portion of the tubular member, which extends from the base portion into an interior portion of the tubular member.

This embodiment additionally comprises a spring located external to and adjacent the support assembly which is capable of resisting vertical downward movement of the assembly toward the base portion of the tubular member. This movement is caused due to the downward pressure exerted by the drill during the formation of the orifice.

Additionally, a collar member surrounds an upper surface of a bit portion of the drill so as to facilitate rotation of the bit portion within the sleeve. The collar member has grooved portions extending longitudinally along an outer periphery thereof in order to facilitate insertion of the bit portion within the collar member.

Further, in this embodiment, three legs of equal length extend from and are formed integrally with a lower surface of the base portion of the tubular member. Each of these legs terminates in a free end, the free ends forming an equilateral triangle. The legs are adapted to rest unsecured upon the cranium. The tubular member, the support assembly and the legs are related to each other and to the cranium in a direction perpendicular to an imaginary plane defined by a tangent to the cranium.

In yet a further embodiment of the invention, an apparatus is disclosed for safely and accurately guiding a drill bit during drilling of an orifice in a cranium. In this embodiment, the apparatus includes a drive shaft; means for securing a drill bit; clutch means for rotatably coupling the drive shaft with the drill bit securing means; and a housing having means for supporting the apparatus on the cranium such that a longitudinal axis of the apparatus is perpendicular to an imaginary plane defined by a tangent to the cranium at the orifice to be drilled; and a coil spring surrounding the clutch means for restricting forward movement of the clutch means along the longitudinal axis of the apparatus. In this embodiment, the clutch means is designed to uncouple the drive shaft from the drill bit securing means when a first end of the drill bit has penetrated the cranium, thereby preventing subsequent rotation and forward movement of the drill bit.

The drive shaft, in this embodiment, includes an upper end adapted to engage a rotary drive unit, such as a surgical drill, and a hollow lower end having a pair of diametrically opposed recesses. The drill bit securing means, on the other hand, includes an upper end adapted to mate with the hollow lower end of the drive shaft, the upper end also having a pair of diametrically opposed openings, and a lower end adapted to receive and secure a drill bit.

The clutch means includes a resilient means positioned between the drive shaft and the drill bit securing means, a first tubular member surrounding the drive shaft, a retaining pin, and a second tubular member surrounding the first tubular member.

The resilient means is preferably a clutch spring which is positioned between the lower end of the drive shaft and the upper end of the drill bit securing means. The purpose of this spring is to urge the securing means from engagement with the drive shaft.

The first tubular member is equipped with a retaining flange for bracing the coil spring within the housing, and a sleeve portion having a pair of diametrically opposed openings and a plurality of sprocket members equipped with outwardly extending sprockets, the sprocket members being separated from one another by ring members. The clutch means further includes a retaining pin which is insertable through the first tubular member openings, through the drill bit securing means openings and the drive shaft recesses. The retaining pin rotatably couples the first tubular means with the drill bit retaining means and the drive shaft.

The second tubular member similarly includes a plurality of ratchet members having inwardly extending ratchet teeth. The ratchet teeth matingly engage the sprockets of the sprocket members. In this embodiment, upon penetration of the cranium by a first end of the drill bit, the resilient means urges the drill bit securing means away from the drive shaft a sufficient distance to disengage the retaining pin from the drive shaft recesses. This uncouples the drive bit securing means from the drive shaft thereby preventing further rotation of the drill bit. Moreover, the ratchet teeth are designed to engage the ring members separating the sprocket members to prevent forward movement of the drill bit securing means into the cranium as soon as the drill bit stops rotating. Thus, this embodiment prevents injury caused by subsequent rotation and plunging of a drill bit into the brain tissue once a first end of the drill bit has penetrated the cranium.

A further embodiment of the invention comprises a method for drilling an orifice in a human cranium at an angle of substantially 90° to a plane defined by a tangent to the cranium at the orifice. The method comprises positioning a drill guide as described below upon a portion of an outer surface of the cranium such that a tubular member of the guide is oriented at an angle of substantially 90° to a plane defined by a tangent to the cranium at the surface thereof.

The guide described herein comprises ring means comprising a retaining member, configured and adapted for engagement with a terminal portion of a flexible spring member and fabricated from a self-lubricating thermoplastic composition; a sleeve member, also fabricated from a self-lubricating thermoplastic, having an open tubular body portion, the body portion comprising a first end, a second end and a circular flange located along an outer peripheral portion of the first end. The sleeve is insertable within the retaining member to form a support assembly. This assembly is capable of a restricted degree of vertical, slideable movement within a tubular member. A tubular member is located adjacent and external to the ring means and is adapted to guide and support these means.

Further, a flexible member is located adjacent the ring means for restricting vertical movement within the tubular member. Support means comprising a plurality of leg members are also provided upon the tubular member. These leg members are adapted to rest unsecured upon the cranium. The support means, the tubular member and the ring means are related to each other and to the cranium so as to guide the drill through the cranium in a direction perpendicular to a plane defined by a tangent to the cranium.

The method further comprises drilling an orifice in the cranium by inserting a drill through the drill guide and pressing downwardly therewith upon the cranium until a bit portion of the drill passes therethrough. The orifice extends through the cranium at an angle of substantially 90° to a plane defined by a tangent to the cranium at the orifice.

In the method described above, the drilling of the cranium may be performed pneumatically, electrically or hydraulically. Further, the method may additionally comprise limiting the depth of penetration of the drill to a predetermined distance within the cranium. This drilling depth is limited by equipping the drill with a clutch for disengaging a bit portion of the drill once a tip of the bit portion has passed through the cranium.

A further embodiment of the method of the invention comprises an alternate method for drilling an orifice in a human cranium at an angle of substantially 90° to a plane defined by a tangent to the cranium at the orifice. The method comprises positioning a drill guide apparatus upon a portion of an outer surface of the cranium such that a tubular member of the guide is oriented at an angle of substantially 90° to a plane defined by a tangent to the cranium at the surface.

The apparatus comprises: a retaining ring, configured and adapted for engagement with a terminal portion of a flexible spring member and fabricated of a self-lubricating thermoplastic composition; a sleeve also fabricated from a self-lubricating thermoplastic, having an open tubular body portion, the body portion comprising a first end a second end and a circular flange located along an outer peripheral portion of the first end. The sleeve is insertable within the retaining ring to form a support assembly. This assembly is capable of a restricted degree of vertical, slideable movement within a tubular member.

The apparatus further comprises a tubular member adjacent and external to the support assembly, adapted to guide and support the assembly. The tubular member has means to direct the vertical, slideable movement of the assembly. This directing means comprises a smooth, cylindrical surface, formed integrally with a base portion of the tubular member, which extends from the base portion into an interior portion of the tubular member.

In addition, a spring is located external to and adjacent the support assembly. This spring is capable of resisting vertical downward movement of the assembly toward the base portion of the tubular member. This movement is caused due to the downward pressure exerted by the drill during the formation of the orifice.

Additionally, a collar member surrounds an upper surface of a bit portion of the drill so as to facilitate rotation of the bit portion within the sleeve. The collar member has grooved portions extending longitudinally along an outer periphery thereof in order to facilitate insertion of the bit portion within the collar member.

Further, in this embodiment, three legs of equal length extend from and are formed integrally with a lower surface of the base portion of the tubular member. Each of these legs terminates in a free end, the free ends forming an equilateral triangle. The legs are adapted to rest unsecured upon the cranium. The tubular member, the support assembly and the legs are related to each other and to the cranium in a direction perpendicular to an imaginary plane defined by a tangent to the cranium.

The method further comprises drilling an orifice in the cranium by inserting a drill through drill guide means described above and pressing it downwardly upon the cranium until a bit portion of the drilling means passes therethrough. The orifice therefore extends through the cranium at an angle of substantially 90° to a plane defined by a tangent to the cranium at the orifice.

DETAILED DESCRIPTION OF THE PREFERRED EMBODIMENTS

Figures 1, 3:
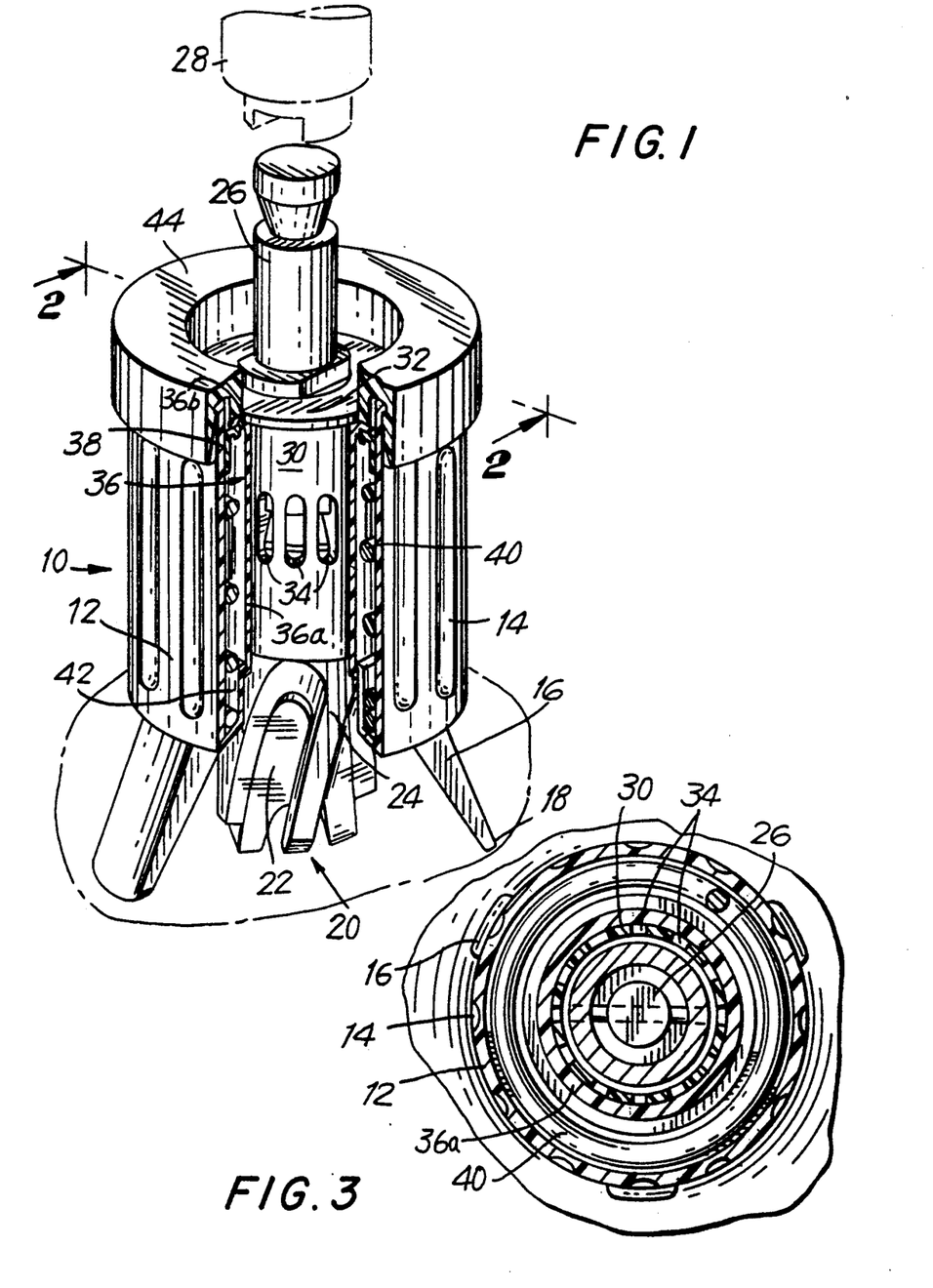
FIG. 1 is a perspective view, partially broken away, illustrating the various components of applicants' drill guide.
FIG. 3 is a cross sectional view of applicants' drill guide, taken along lines 3—3 of FIG. 2.

Referring initially to FIG. 1 there is illustrated a view, partially broken away, of applicant's drill guide 10. Guide 10 comprises tubular member 12 having a plurality of indented portions 14 along an outer peripheral portion thereof. Portions 14 thus provide a convenient grip for the surgeon to ensure that guide 10 does not slip during the drilling procedure. Tubular member 12 is preferably formed by molding from an engineering thermoplastic such as Delrin ®, ABS, an acrylic, etc.

Guide 10 is supported on a plurality of leg members 16, preferably three in number, formed integrally with and extending from a lower surface (not shown) of tubular member 12. Each of legs 16 terminates in a free end 18, the free ends forming a polygon upon the surface of the patient's cranium, thus defining a plane.

Drill bit 20, comprising an inner sleeve 22 and an outer sleeve 24 is guided in a direction perpendicular to the subject plane and through the geometric center of the polygon. In instances where guide 10 is supported by three legs 16 of equal length, (as described above) the polygon thus formed is an equilateral triangle.

Drill bit 20 is provided with stud 26 on its upper surface for insertion within a housing 28 of a surgical drill apparatus. It must be noted, however, that the drill apparatus, of itself, is known in the art and does not form any part of the invention. As described in the background art section of the present application, commonly utilized surgical drills, such as those manufactured by the Codman & Shurtleff, Inc. of Randolph, Mass. and the Accracut Company of Acton, Mass., are provided with a safety clutch mechanism. Clutches of this type offer a built-in safety feature in which the drill automatically stops rotating once the pressure upon the tip of the drill bit is released, i.e., once the drill bit passes through the cranium.

Drill bit 20 is encased in collar member 30. Collar 30 serves to keep inner shaft 22 and outer shaft 24 of drill bit 20 in the proper alignment and prevent the pin member (not shown) which holds the drill bit together from falling out during the drilling operation. Collar member 30 is formed with flange 32 upon an upper surface thereof, the function of which is discussed below. Further, collar 30 is also provided with peripherally distributed longitudinal grooves 34 which enable collar 30 to balloon outwardly in order to permit the passage of drill bit 20 upon the insertion thereof. Once bit 20 is slipped into collar member 30, the rippled surface on the inner portion of collar 30, especially in the zone of grooved portions 34, prevents drill bit 20 from sliding back out of collar 30 (see, e.g., FIGS. 2 and 4).

Collar 30, surrounding drill bit 20, rests inside sleeve member 36. Sleeve 36 comprises an open tubular body portion 36a having a first end and a second end and an integrally formed circular flange member 36b located along an outer peripheral portion of the first, i.e., upper, end. Sleeve member 36 is preferably fabricated from a self-lubricating thermoplastic composition, such as Teflon ® or Nylex ®, for example, in order to facilitate vertical movement of the sleeve within tubular member 12. In addition, flange 32 on the upper surface of collar member 30 is adapted to rest upon flanged portion 36b of sleeve member 36.

Drill guide 10 additionally comprises retainer member 38 which is constructed as a ring-shaped member positioned beneath flange 36b of sleeve member 36. Member 38 rests atop spring 40 and acts to retain at least an upper portion of spring 40 within tubular member 12. A lower portion of spring 40 is supported within directing means 42, which additionally serves to direct, i.e., prevent, any horizontal oscillation by sleeve member 36 as it slides vertically within the bore of tubular member 12.

Directing means 42 is formed integrally with a base, i.e., lower, portion of tubular member 12 and it extends inwardly from the base portion into said bore. Directing means 42 thus serves a two-fold purpose, i.e., (1) it provides a support for the lower portion of spring 40, and (2) it extends upwardly within the bore of tubular member 12, slightly beyond the lower edge of body portion 36a of sleeve member 36 when spring 40 is in an uncompressed state. This arrangement ensures that the lower peripheral edge of body portion 36a can not catch upon the upper edge of directing means 42 as a result of any horizontal oscillation by bit assembly 20 as assembly 20 is pushed downwardly within tubular member 12 during the drilling operation.

Drill guide 10 may additionally be provided with cap member 44 capable of snap locking engagement with an upper surface of tubular member 12. Cap 44 prevents the various components of guide 10 from falling out of tubular member 12 in the event guide 10 is turned upside down.

Figure 2:
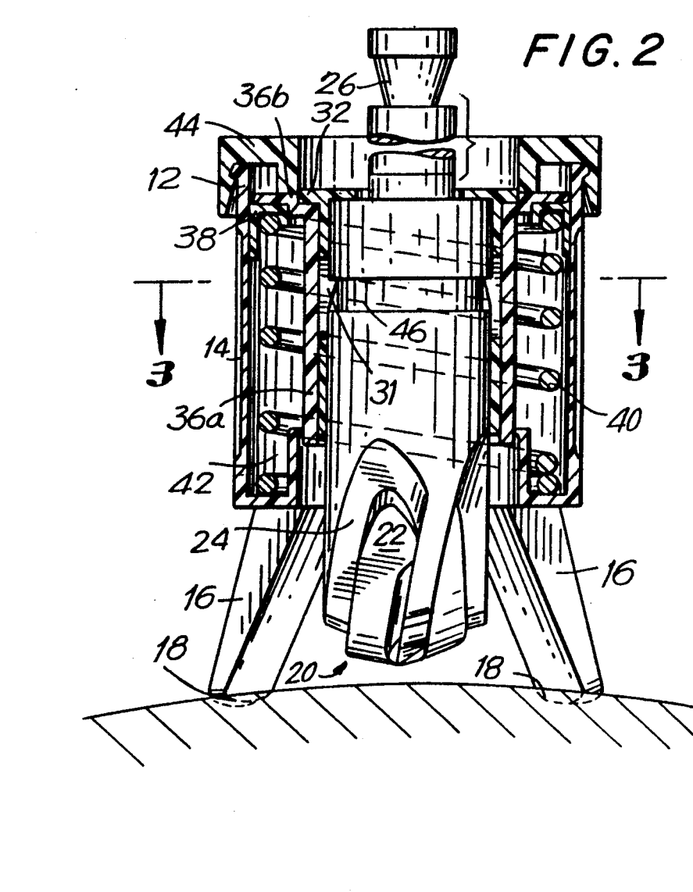
FIG. 2 is a sectional view of applicants' drill guide with the drill bit in the raised position, taken along line 2—2 of FIG. 1.

Turning now to FIG. 2, there is illustrated a cross-sectional view of drill guide apparatus 10 of the present invention with bit 20 in place, but prior to the engagement of the drilling device therewith. Since many of the features displayed in the subject drawing figure are the same as those discussed above with regard to FIG. 1, they have been labeled with the same numerical designation in order to prevent any confusion.

FIG. 2 illustrates more clearly the arrangement of parts discussed above with respect to FIG. 1 wherein collar member 30 surrounds an upper portion of drill bit 20 while inserted within sleeve member 36, which rests atop retainer ring 38. Thus, flange 36b of sleeve member 36 is sandwiched between flange 32 of collar member 30 and the upper surface of retainer member 38.

In addition, this view more clearly illustrates the means by which drill bit 20 is retained within collar member 30. For this purpose, the inner surface of grooved portions 34 in collar member 30 is provided with tangs 31 which engage an indented portion 46 of the bit mechanism. As noted above, this prevents the removal of bit 20 from collar member 30 unless grooved portions 34 are squeezed sufficiently tightly to cause collar 30 to balloon outwardly, thus releasing tangs 31 from indented portion 46. This action requires the use of specialized tools such as a drill press and will not occur during normal drilling operations.

FIG. 3 is a cross-sectional view of guide apparatus 10 taken through line 3—3 of FIG. 2. This view further illustrates the internal arrangement of the components which comprise guide 10.

Figure 4:
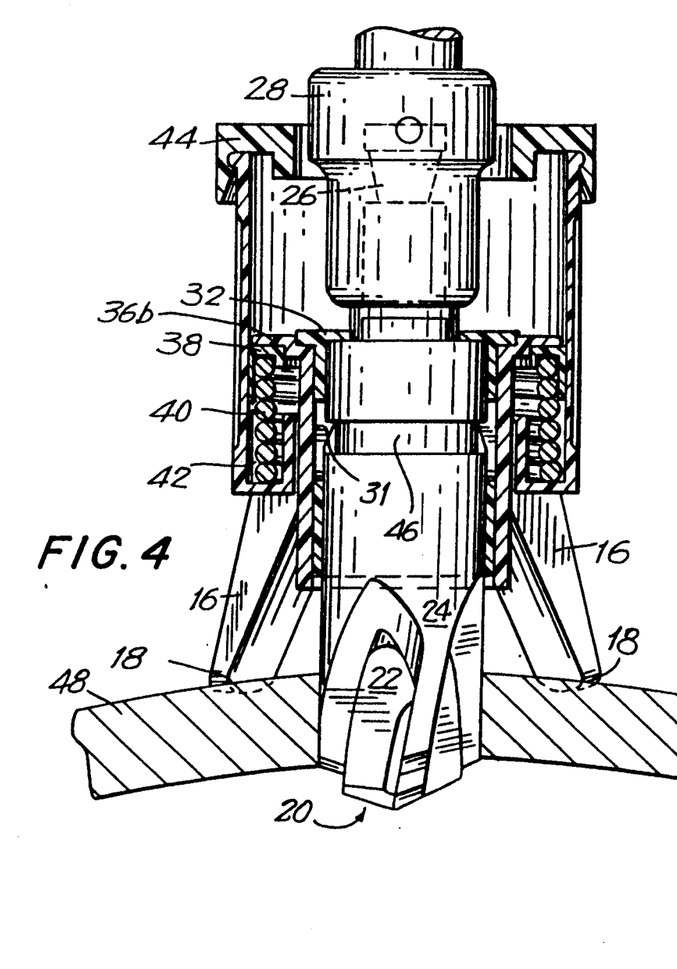
FIG. 4 is a view similar to that of FIG. 2 illustrating the operation of applicants' drill guide as described herein.

Turning now to FIG. 4, there is illustrated a view of guide 10 in operation, i.e. with the drilling device coupled to drill bit 20. Again, those features which are shown and described in FIGS. 1, 2 and 3 are designated with the same numbers as used previously. FIG. 4 illustrates the formation of a burr hole through cranium 48 wherein the drilling apparatus is inserted downwardly through guide 10 and housing 28 is coupled to an upper portion 26 of bit 20.

As the drill is pressed into cranium 48, flange 32 of collar member 30, positioned atop flange 36b of sleeve member 36, forces sleeve member 36 downwardly upon retainer member 38. As member 38 is forced down, it causes spring 40 to compress within directing means 42. Once spring 40 is compressed to its maximum limit, the drill can proceed no further in a downwardly direction. Applicants' guide 10 has been designed such that, when spring 40 is completely compressed, the tip of inner sleeve 22 of drill bit 20 is barely exiting the surface of the patient's skull (if of maximum thickness) into the inner cranial cavity. As an added safety factor, and in view of the fact that different patients have skull of different thicknesses, the drills utilized by applicants with guide 10 are equipped with the safety clutch feature described above.

With regard to the drill itself, one can utilize an electrically or hydraulically operated apparatus, however, applicants have achieved good success with pneumatically operated drills as described above with reference to the commonly available types of drills available to most practicing neurosurgeons.

Turning now to FIGS. 5 through 9 there is illustrated a second embodiment of the applicants' invention generally designated by the numeral 100 and including therein an integral safety clutch. Apparatus 100 includes a drive shaft 102, means for securing a drill bit 110, clutch means rotatably coupling drive shaft 102 with drill bit securing means 110, a housing 136, and a coil spring 140.

Figure 5:
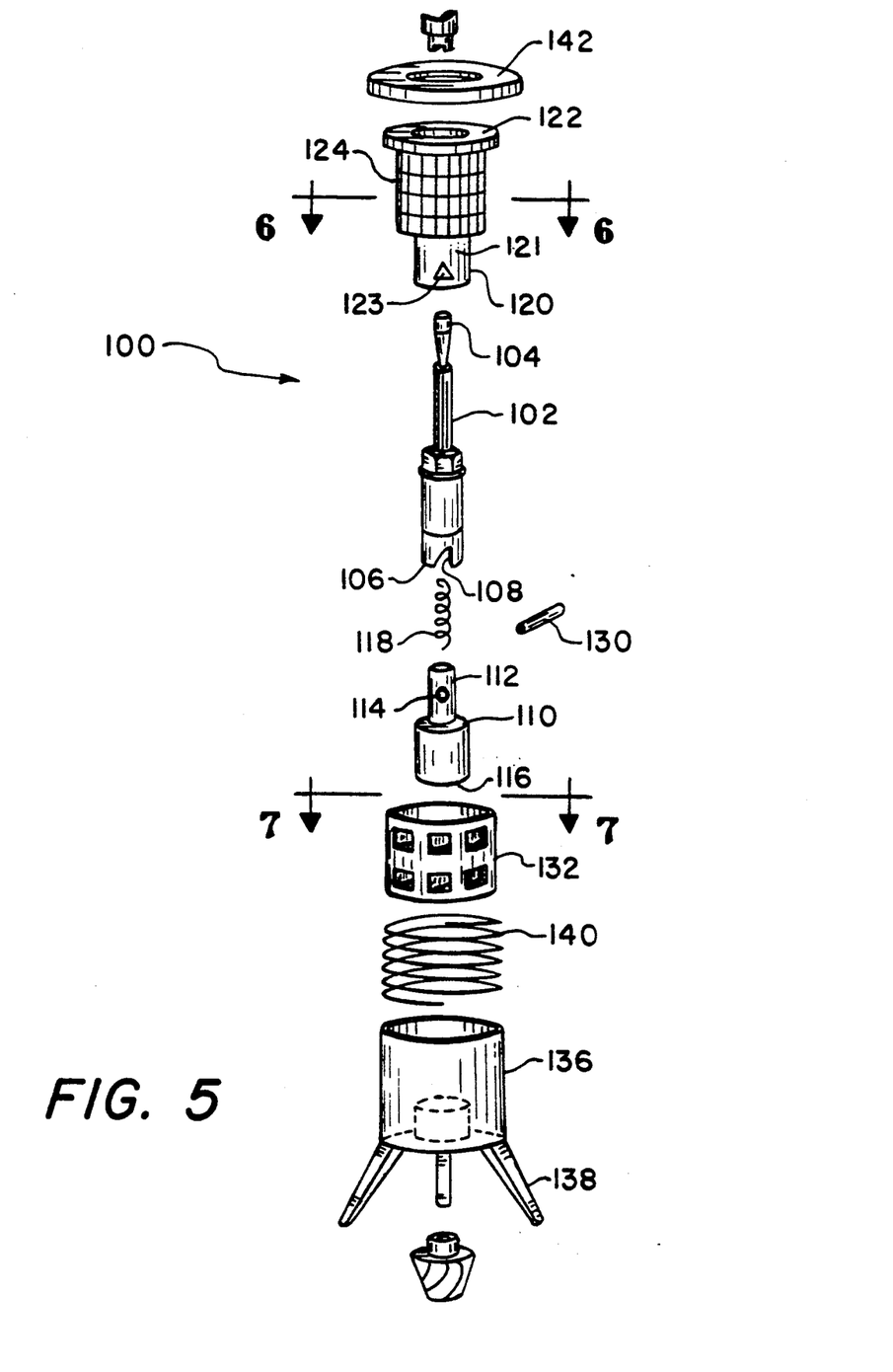
FIG. 5 is an exploded view of a second embodiment of the applicants' drill guide, including a drive shaft, a drill bit securing means and a clutch means.

Drive shaft 102 includes an upper end 104 adapted to engage a rotary drive unit, such as a surgical drill, and a hollow lower end 106 having a pair of diametrically opposed recesses 108. Drill bit securing means 110 is equipped with an upper end 112 adapted to mate with hollow lower end 106 of drive shaft 102, and a lower end 116 adapted to receive and secure one end of a drill bit. Upper end 112 of drill bit securing means 110 further includes a pair of diametrically opposed openings 114.

The clutch means of the present invention includes resilient means 118 positioned between drive shaft 102 and drill bit securing means 110, a first tubular member 120 surrounding drive shaft 102, a retaining pin 130 and a second tubular member 132 surrounding first tubular member 120.

Figure 6:
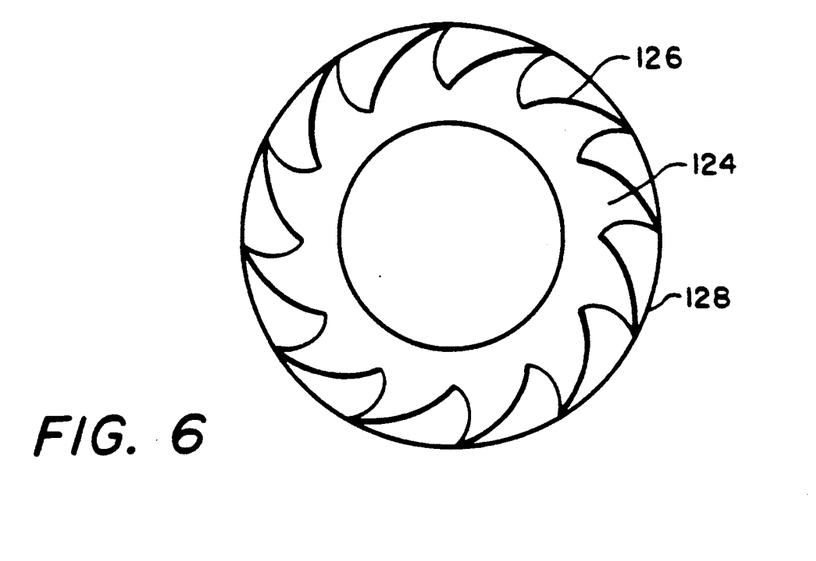
FIG. 6 is a sectional view of a sprocket member of the clutch means taken along line 6—6 of FIG. 5.

Resilient means 118 is preferably a clutch spring which is positioned between lower end 106 of drive shaft 102 and upper end 112 of drill bit securing means 110. First tubular member 120 includes a sleeve portion 121 and a retaining flange 122 for bracing coil spring 140 within housing 136. Sleeve portion 121 further includes a pair of diametrically opposed openings 123 and a plurality of sprocket members 124. As shown in FIG. 6, sprocket members 124 include a plurality of outwardly extending sprockets 126. Furthermore, sprocket members 124 are separated from one another by ring members 128.

Retaining pin 130 is configured and designed to be insertable through first tubular member openings 123, drill bit securing means openings 114 and drive shaft recesses 108. Retaining pin 130 serves to rotatably couple first tubular member 120, drill bit securing means 110 and drive shaft 102.

Figure 7:
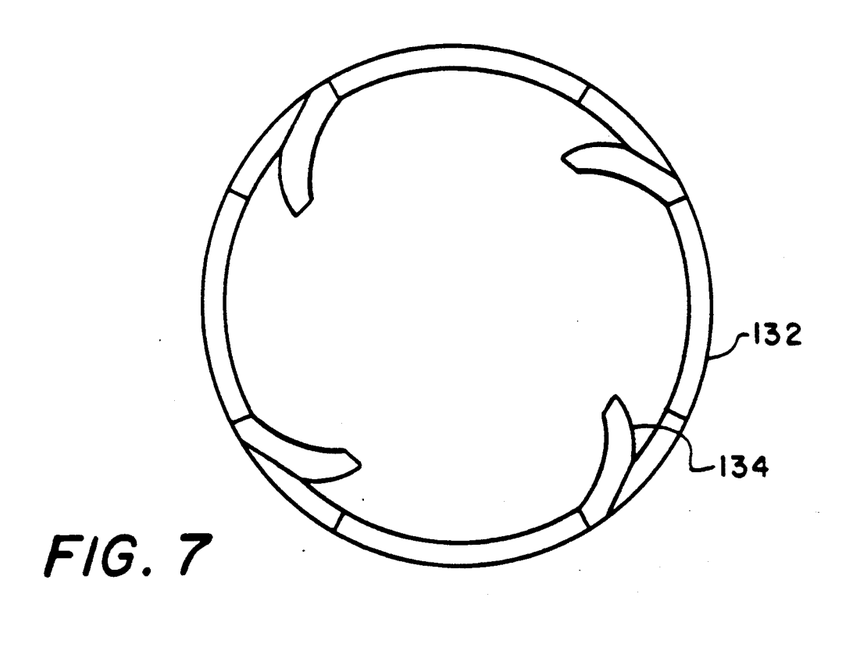
FIG. 7 is a sectional view of a ratchet member of the clutch means, taken along line 7—7 of FIG. 5.
Figure 8:
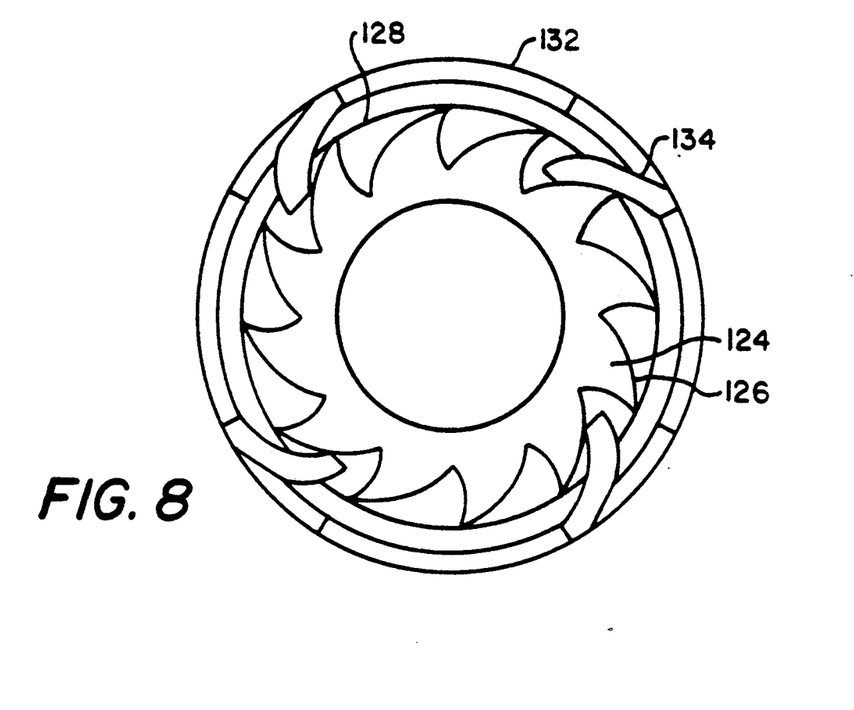
FIG. 8 is a view similar to that of FIG. 7 illustrating the configuration of the ratchet teeth with respect to the sprockets with the drill bit stationary.
Figure 9:
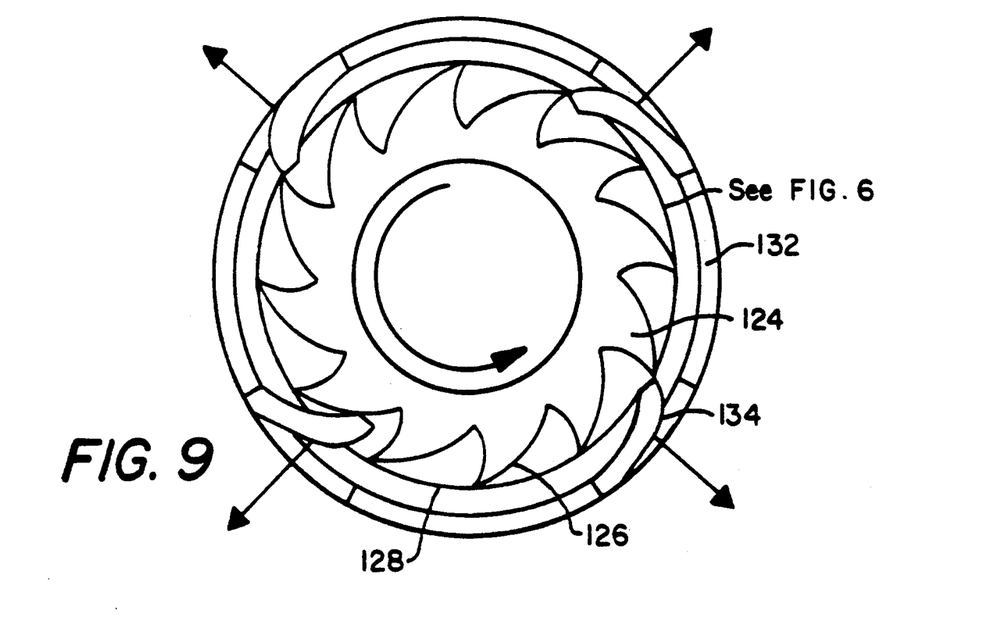
FIG. 9 is a view similar to that of FIG. 8 showing a ratchet member superimposed on a sprocket member during rotation of the drill bit.

Second tubular member 132 includes a plurality of inwardly extending ratchet teeth 134, as best illustrated in FIG. 7. FIG. 8 demonstrates that ratchet teeth 134 are designed and configured to matingly engage sprockets 126 of sprocket members 124 when drive shaft 102 is stationary. As shown in FIG. 9, however, ratchet teeth 134 are sufficiently flexible so that when drive shaft 102 rotates, ratchet teeth 134 are forced outward by sprockets 126 thereby allowing rotation and forward movement of the drill bit.

Housing 136 further includes means 138 for supporting apparatus 100 on the cranium of a patient such that a longitudinal axis of the apparatus is perpendicular to an imaginary plane defined by a tangent to the cranium at the orifice to be drilled. Coil spring 140 which is positioned within housing 136 surrounds the clutch means and restricts forward movement of the clutch means along the longitudinal axis of the apparatus. Coil spring 140 is braced axially between retaining flange 122 of first tubular member 120 and the lower end of housing 136.

Apparatus 100 may additionally be provided with a cap member 142 capable of lockingly engaging an upper surface of housing member 136. Cap 142 prevents the various components of apparatus 100 from falling out of housing member 136 in the event that housing member 136 is turned upside down.

This embodiment is specifically designed to prevent injury to brain tissue caused by the subsequent rotation and forward movement of a drill bit once a first end of the drill bit has penetrated the cranium. To this end, the clutch means of apparatus 100 is designed to uncouple drive shaft 102 from drill bit securing means 110 once a first end of the drill bit has exited the back surface of the cranium. By uncoupling drive shaft 102 and drill bit securing means 110, the clutch means prevents subsequent rotation and forward movement of the drill bit.

By way of illustration, upon penetration of the cranium by the drill bit, the pressure upon the bit is released, in which case coil spring 118 urges drive shaft 102 away from drill bit securing means 110. With no force resisting the separating force supplied by coil spring 118, drive shaft 102 is driven a sufficient distance away from drill bit securing means 110 so that retaining pin 130 disengages from the drive shaft recesses 108. Accordingly, when retaining pin 130 disengages recesses 108, drill bit securing means 110 and drive shaft 102 are no longer coupled, therefore drill bit securing means 110 ceases to rotate. Furthermore, as soon as the drill bit securing means 110 stops rotating ratchet teeth 134 engage ring members 128. As is best seen in FIG. 8, the engagement of ratchet teeth 134 with ring members 128, prevents forward movement of drill bit securing means 110.

One especially advantageous feature of this embodiment, is the unique shape of recesses 108 in drive shaft 102. Recesses 108, are adapted to re-engage retaining pin 130 without removing apparatus 100 from a partially drilled orifice. This feature allows a physician to re-engage or re-couple drive shaft 102 with drill bit securing means 110 while apparatus 100 is in its mounted position upon the cranium. Thus, a physician can stop and start drilling several times without the need to remove the apparatus from the patient's cranium and manually realign and re-couple the drive shaft and the drill securing means.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. An apparatus for accurately and reproducibly guiding drill means during the formation of an orifice in a human cranium, wherein said orifice extends at an angle of substantially 90° to an imaginary plane defined by a tangent to said cranium at said orifice, said apparatus comprising:

(a) ring means comprising a retaining member configured and adapted for engagement with a terminal portion of a spring means and a sleeve member, insertable within said retaining member and operatively associated therewith, said sleeve member comprising an open tubular body portion having a first end and a second end and an integrally formed circular flange member located along an outer peripheral portion of said first end, said ring means capable of a restricted degree of vertical, slideable movement within tubular means and fabricated from a self-lubricating thermoplastic composition to facilitate the movement thereof;

(b) tubular means adjacent and external to said ring means, adapted to guide and support said ring means, said tubular means having means for directing said vertical, slideable movement of said ring means, said directing means comprising channel means formed integral with a base portion of said tubular member entirely around an inner surface thereof and extending into a central bore defined by said tubular member, said channel means configured and adapted for supporting a lower portion of said spring means and having an inner wall portion adjacent said central bore separated from an outer wall portion formed by an inner surface of said tubular member by a base portion positioned substantially perpendicularly to and formed integral with both said inner and said outer wall portions, wherein said inner wall portion extends a sufficient distance within said bore so as to terminate beyond said second end of said open tubular body portion of said sleeve member to prevent any interference between said second end and said inner wall during said vertical slideable movement of said ring means within said tubular means;

(c) spring means located adjacent said body portion of said sleeve member and capable of resisting vertical movement of said ring means toward said base portion of said tubular means caused due to downward pressure exerted by said drill means during the formation of said orifice, said spring means encased within said tubular means (d) a collar member surrounding to an upper surface of a bit portion of said drill means so as to facilitate rotation of said bit portion within said ring means, said collar member having grooved portions extending substantially therethrough to facilitate insertion of said bit portion within said collar member, each said grooved portion comprising, along an inner surface thereof, at least one tang configured and adapted for engaging an outer surface of said bit portion; and (e) a plurality of leg members extending from and formed integrally with a lower surface of said base portion of said tubular means, said leg members adapted to rest unsecured upon an arcuate portion of said cranium, said tubular means, said ring means and said leg members being related to each other and to said cranium so as to guide said drill means through said arcuate portion in a direction perpendicular to an imaginary plane defined by a tangent to said cranium at said arcuate portion.

2. The apparatus of claim 1 wherein each of said plurality of legs terminates in a free end, said free ends forming a polygon defining a plane, said sleeve means guiding said drill means in a direction perpendicular to said plane and through the geometric center of said polygon.

3. The apparatus of claim 2 wherein said support means comprises three legs of equal length and wherein an equilateral triangle is formed by said free ends of said legs.

4. The apparatus of claim 1 further comprising a cap member for interlocking engagement with an upper surface of said tubular means, said cap member having an open bore portion to permit passage of said drill means therethrough.

5. An apparatus for accurately and reproducibly guiding drill means during the formation of an orifice in a human cranium, wherein said orifice extends at an angle of substantially 90° to an imaginary plane defined by a tangent to said cranium at said orifice, said apparatus comprising:

(a) a retaining ring, configured and adapted for engagement with a terminal portion of a flexible spring and fabricated from a self-lubricating thermoplastic composition;

(b) a sleeve fabricated from a self-lubricating thermoplastic composition, said sleeve comprising an open tubular body portion having a first end and a second end and an integrally formed circular flange located along an outer peripheral portion of said first end, said sleeve further insertable within said retaining ring to form a support assembly, said support assembly capable of a restricted degree of vertical, slideable movement within tubular means;

(c) tubular means, adjacent and external to said support assembly, said tubular means adapted to guide and support said sleeve and said retaining ring, said tubular means having means for directing said vertical, slideable movement of said support assembly, said directing means comprising channel means formed integral with a base portion of said tubular member entirely around an inner surface thereof and extending into a central bore defined by said tubular member, said channel means configured and adapted for supporting a lower portion of said flexible spring and having an inner wall portion adjacent said central bore separated from an outer wall portion formed by an inner surface of said tubular member by a base portion positioned substantially perpendicularly to and formed integral with both said inner and said outer wall portions, wherein said inner wall portion extends a sufficient distance within said bore so as to terminate beyond said second end of said open tubular body portion of said sleeve member to prevent any interference between said second end and said inner wall during said vertical slideable movement of said ring means within said tubular means;

(d) a spring located adjacent said support assembly and capable of resisting vertical movement of said support assembly toward said base portion of said tubular means caused due to downward pressure exerted by said drill means during the formation of said orifice, said spring encased within said tubular means;

(e) a collar member surrounding an upper surface of a bit portion of said drill means so as to facilitate rotation of said bit portion within said sleeve said collar member having grooved portions extending longitudinally therethrough to facilitate insertion of said bit portion within said collar member, each said grooved portion comprising, along an inner surface thereof, at least one tang configured and adapted for engaging an outer surface of said bit portion; and (f) three legs of equal length extending from and formed integrally with a lower surface of said base portion of said tubular means, each of said legs terminating in a free end, said free ends forming an equilateral triangle, said legs adapted to rest unsecured upon an arcuate portion of said cranium; said tubular means, said support assembly and said legs being related to each other and to said cranium so as to guide said drill means through said arcuate portion in a direction perpendicular to an imaginary plane defined by a tangent to said cranium at said arcuate portion.

6. The apparatus of claim 5 wherein said tubular means further comprises a plurality of substantially vertical indented portions along an outer circumferential periphery thereof, said indented portions configured and adapted to facilitate non-slip gripping of said apparatus.

7. The apparatus of claim 6 wherein said tubular means is molded from an engineering thermoplastic selected from among Delrin ®, ABS and an acrylic.

8. The apparatus of claim 5 wherein said self-lubricating thermoplastic composition is selected from the group consisting of Teflon ® and Nylex ®.

9. The apparatus of claim 1 further comprising an annular cap member configured for interlocking engagement with an upper peripheral surface of said tubular means, said cap member having an open bore portion to permit passage of said drill means therethrough.

10. The apparatus of claim 5 which further comprises a drill adapted for rotating said bit portion, at least a portion of said drill configured for insertion within said open tubular body portion of said sleeve.

11. The apparatus of claim 10 wherein said drill is selected from among electric, hydraulic and pneumatic surgical drills.

12. An apparatus for accurately and reproducibly guiding drill means during the formation of an orifice in a human cranium, wherein said orifice extends at an angle of substantially 90° to an imaginary plane defined by a tangent to said cranium at said orifice, said apparatus comprising:

(a) a retaining ring, configured and adapted for engagement with a terminal portion of a flexible spring and fabricated from a self-lubricating thermoplastic composition;

(b) a sleeve fabricated from a self-lubricating thermoplastic composition, said sleeve comprising an open tubular body portion having a first end and a second end and an integrally formed circular flange located along an outer peripheral portion of said first end, said sleeve further insertable within said retaining ring to form a support assembly, said support assembly capable of a restricted degree of vertical, slideable movement within tubular means;

(c) tubular means, adjacent and external to said support assembly, said tubular means adapted to guide and support said sleeve and said retaining ring, said tubular means having means for directing said vertical, slideable movement of said support assembly, said directing means comprising channel means formed integral with a base portion of said tubular member entirely around an inner surface thereof and extending into a central bore defined by said tubular member, said channel means configured and adapted for supporting a lower portion of said flexible spring and having an inner wall portion adjacent said central bore separated from an outer wall portion formed by an inner surface of said tubular member by a base portion positioned substantially perpendicularly to and formed integral with both said inner and said outer wall portions wherein said inner wall portion extends a sufficient distance within said bore so as to terminate beyond said second end of said open tubular body portion of said sleeve member to prevent any interference between said second end and said inner wall during said vertical slideable movement of said ring means within said tubular means;

(d) a spring located adjacent said support assembly and capable of resisting vertical movement of said support assembly toward said base portion of said tubular means caused due to downward pressure exerted by said drill means during the formation of said orifice;

(e) a collar member surrounding an upper surface of a bit portion of said drill means so as to facilitate rotation of said bit portion within said sleeve, said collar member having grooved portions extending longitudinally therethrough to facilitate insertion of said bit portion within said collar member, each said grooved portion comprising, along an inner surface thereof, a tang configured and adapted for engaging an outer surface of a bit portion of said drill means; and (f) three legs of equal length extending from and formed integrally with a lower surface of said base portion of said tubular means, each of said legs terminating in a free end, said free ends forming an equilateral triangle, said legs adapted to rest unsecured upon an arcuate portion of said cranium; said tubular means, said support assembly and said legs being related to each other and to said cranium so as to guide said drill means through said arcuate portion in a direction perpendicular to an imaginary plane defined by a tangent to said cranium at said arcuate portion.

* * * * *